United States Patent
Blank et al.

(10) Patent No.: US 8,663,552 B2
(45) Date of Patent: Mar. 4, 2014

(54) METHOD FOR TREATING A MEDIUM BY SATURATING IT WITH USEFUL SUBSTANCES EMITTED BY PLANTS AND A DEVICE FOR CARRYING OUT THIS METHOD

(76) Inventors: Pol' Emanuilovich Blank, Moscow (RU); Emanuil Ihilovich Blank, Moscow (RU)

(*) Notice: Subject to any disclaimer, the term of this patent is extended or adjusted under 35 U.S.C. 154(b) by 185 days.

(21) Appl. No.: 13/262,651

(22) PCT Filed: Apr. 7, 2010

(86) PCT No.: PCT/RU2010/000162
§ 371 (c)(1),
(2), (4) Date: Oct. 3, 2011

(87) PCT Pub. No.: WO2010/117307
PCT Pub. Date: Oct. 14, 2010

(65) Prior Publication Data
US 2012/0132285 A1    May 31, 2012

(30) Foreign Application Priority Data
Apr. 8, 2009 (RU) ................ 2009113049

(51) Int. Cl.
*A61L 9/00* (2006.01)
*A61L 2/00* (2006.01)

(52) U.S. Cl.
USPC ........ 422/5; 422/1; 422/28; 422/32; 422/292; 422/305

(58) Field of Classification Search
USPC ............... 422/1, 5, 28, 32, 292, 305
See application file for complete search history.

(56) References Cited

U.S. PATENT DOCUMENTS

| 6,187,263 B1 | 2/2001 | Nielsen |
| 7,534,350 B2 | 5/2009 | Blank et al. |

FOREIGN PATENT DOCUMENTS

| EA | 010104 | 6/2008 | |
| RU | 2 143 922 | 1/2000 | |
| RU | 2 288 009 | 10/2006 | |
| RU | 2 305 588 | 9/2007 | |
| RU | 200700943 | * 6/2008 | ............ A61K 36/00 |
| SU | 1716268 | 2/1992 | |

OTHER PUBLICATIONS

European Patnent Office Englsih translation of the Description section of EA 200700943.*

(Continued)

*Primary Examiner* — Monzer R Chorbaji
(74) *Attorney, Agent, or Firm* — Collard & Roe, P.C.

(57) ABSTRACT

The invention relates to the saturation of different gaseous, liquid, gel-like, solid and mixed media with ingredients emitted by vegetative plants. The method for treating a medium by saturating it with useful substances emitted by plants involves supplying a gaseous medium to a chamber containing vegetative or cut plants and passing the gaseous medium saturated with plant excreta through the medium undergoing treatment. Furthermore, a low pressure or a low and a high pressure is generated in the above-mentioned gaseous medium in the chamber containing the vegetative or cut plants. The medium treating device comprises a means for pumping the gaseous medium, at least one chamber for plants emitting plant excreta, which chamber is connected by a pipe to the above-mentioned means on the intake side and to the pumping means on the discharge side; furthermore, the above-mentioned means is connected on the discharge side to at least one container for the medium undergoing treatment.

6 Claims, 1 Drawing Sheet

(56) References Cited

OTHER PUBLICATIONS

Gahrns, H.-H., Technische Belüftung steigert Effektivität der Forellenproduktion (Use of Aeration in Bodies of Water for Trout Breeding); Z. Binnenfischerei DDR, 1988, vol. 35, No. 6, pp. 209-214. (Spec, p. 1).

Kindschi, G. A., Notes on Two Feed Types and Methods for Steelhead Trout Production; Program. Fish-Culturist, 1984, vol. 46, No. 1, pp. 44-47. (Spec, p. 1).

Rümmler, F., Pfeifer, M., Erste Versuche zur $K_{1-2}$-Produktion in einer Anlage mit Sauerstoffbegassung and Rundbecken (First Experiments to Breed One- and Two-Year-Old Carps in Oxygen-Rich Round Pools), Z. Binnenfischerei DDR, 1987, vol. 34, No. 6, pp. 179-185). (Spec, p. 1).

International Search Report of PCT/RU2010/000162, Aug. 19, 2010.

* cited by examiner

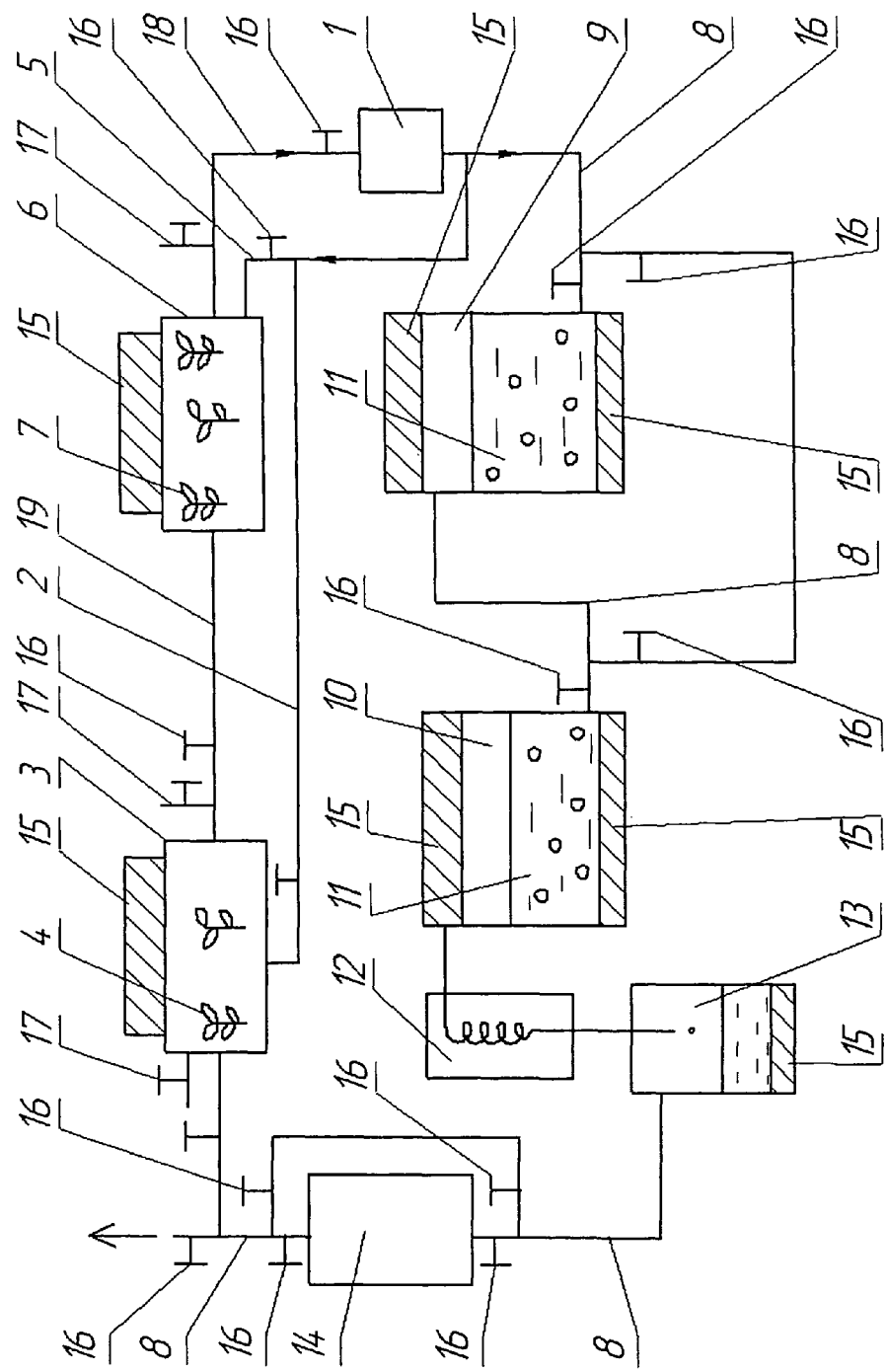

METHOD FOR TREATING A MEDIUM BY SATURATING IT WITH USEFUL SUBSTANCES EMITTED BY PLANTS AND A DEVICE FOR CARRYING OUT THIS METHOD

CROSS REFERENCE TO RELATED APPLICATIONS

This application is the National Stage of PCT/RU2010/000162 filed on Apr. 7, 2010, which claims priority under 35 U.S.C. §119 of Russian Application No. 2009113049 filed on Apr. 8, 2009, the disclosure of which is incorporated by reference. The international application under PCT article 21(2) was not published in English.

FIELD OF THE INVENTION

The invention relates to the saturation of various gaseous, liquid, gel-like, solid, including powdered, and mixed mediums with ingredients released by vegetating plants, and may be used for improving the environment of offices, dwellings, and bodies of water, in the food industry, pharmaceutics, fisheries and agriculture, including air quality improvement indoors, for preparing beverages, foodstuffs and additives, drugs, perfumery and cosmetics, for inhalations, bathing, improving the resistance and productivity of fish species and other useful animals and microorganisms, and for preparing plant treatment means.

BACKGROUND OF THE INVENTION

Methods and devices for modifying the quality of water, liquids, and other substances by purifying them, or supplying, pumping (aerating under pressure), or passing air and other gases through the same are known in prior art (Gahrns, H.-H., Technische Beluftung Steigert Effectivitat der Forellenproduktion (Use of Aeration in Bodies of Water for Trout Breeding) [1]; Z. Binnenfiseherei DDR, 1988, Vol. 35, No. 6, pp. 209-214[1]; Kindschi, G. A., Notes on Two Feed Types and Methods for Steelhead Trout Production [2]; Program. Fish-Culturist, 1984, Vol. 46, No. 1, pp. 44-47[2]; Rummler, F., Pfeifer, M., Erste Versuche zur K (1-2)—Produktion in einer Anlage mit Sauerstoffbegassung and Rundbecken (First Experiments to Breed One- and Two-Year-Old Carps in Oxygen-Rich Round Pools), Z. Binnenfiseherei DDR, 1987, Vol. 34, No. 6, pp. 179-185) [3].

The prior art methods and devices are disadvantageous because of the inadequate all-around result due to a limited selection of effective substances and unrecoverable (nonrenewable naturally) use of some important components (for example, oxygen), fillers, filter materials, and so on.

Another prior art method is used to make indoor air healthier by placing vegetating plants releasing volatile organic substances indoors (Russian Federation Patents No. 2,143,922 and No. 2,288,009).

This prior art method is suited for a limited purpose of making indoor air healthier to breathe.

The prior art method closest to the present invention comprises treating a liquid medium by passing a flow of oxygen-containing gaseous medium pre-saturated with phyto-excretions of vegetating or cut plants through the liquid medium, the gaseous medium being saturated with phyto-excretions of plants by passing the flow of said medium through a chamber containing plants releasing phyto-excretions. Before the gaseous medium is saturated with phyto-excretions, it is purified to remove harmful impurities by passing the flow of said medium through an additional chamber containing vegetating and/or cut plants that absorb the objectionable harmful impurities. Release of phyto-excretions is intensified by subjecting the plants to heat, and/or light, and/or sound, and/or electromagnetic force. The device for treating a liquid medium comprises means for pumping a gaseous medium having a delivery and suction pipes, at least one tank for the liquid medium, at least one chamber containing plants releasing phyto-excretions, the delivery pipe of said means being connected to the liquid medium tank, and the suction pipe being connected to the chamber containing plants releasing phyto-excretions. The device is provided with at least one chamber containing plants that absorb impurities and connected to the chamber containing plants that release phyto-excretions. The chambers with plants and the liquid medium tanks are provided with devices used to adjust at least one of the environments—aqueous, gaseous, food, and light—and at least one type of plant treatment—chemical, sonic, light, or electromagnetic (EA 010104, published Jun. 30, 2008). In the prior art method the gaseous medium is constantly pumped through the chamber containing plants releasing phyto-excretions through opened valves, therefore the plants in the chamber are under atmospheric pressure.

The prior art method is disadvantageous because of the limited opportunities offered by heat, light, and electromagnetic force to control the release of phyto-excretions by vegetating plants.

SUMMARY OF THE INVENTION

It is an object of the present invention to increase significantly the release of phyto-excretions by plants and, in need, maintain a high release intensity after the effect of the stimulating environment factors has been reduced.

This object is achieved in a method for treating a medium by saturating it with useful substances released by plants, said method including supply of a gaseous medium into a chamber containing vegetating or cut plants and passing the gaseous medium saturated with phyto-excretions through the medium being treated such that, according to the invention, the pressure of said gaseous medium in the chamber containing vegetating or cut plants is reduced or raised and then reduced periodicall.

It is preferred to supply the gaseous medium initially to another chamber containing plants that absorb harmful substances and to build up excess pressure of said gaseous medium in said other chamber.

The medium being treated may be a gaseous medium, or liquid, or solid medium in the form of powder, or granules, or sorbent.

The object of the invention is also achieved in a device for carrying out the present method, said device comprising means to pump the gaseous medium to at least one chamber for plants releasing phyto-excretions that is connected by a pipeline to said means at the suction side thereof, said means communicating at the delivery side thereof with at least one receptacle for the medium being treated, such that, according to the invention, at least one chamber for plants releasing phyto-excretions is also connected by a pipeline to the pumping means at the delivery side thereof.

The device may also be provided with at least one chamber for plants absorbing harmful substances, said chamber being connected by pipelines to the chamber for plants releasing phyto-excretions and to said means at the delivery side thereof.

The receptacle for the medium being treated may be a tank or a room.

The invention is based on the idea of saturating gaseous, liquid, solid, and mixed mediums with useful substances released by plants, in addition to oxygen.

It was established, in a series of experiments, that the medium saturated hereunder acquires the useful qualities of substances released by plants.

Phyto-excretions are the end products of metabolism that are discharged out of plants. Plant excretion involves glands and cell surface, and excretions are washed down passively by rain and mostly evaporated.

Terpenoids (terpenes) predominate among phyto-excretions. Terpenoids are natural hydrocarbons of formula $C_{10}H_{16}$, and their numerous oxygen derivatives (alcohols, aldehydes, ketones, acids, oxides, and so on). They are contained mostly in the essential oils of flowers, leaves, conifer needles, plant fruits, various natural resins (balsams), and conifer trees (pine, fir, cedar, spruce, and so on).

Terpenoids are different from other organic compounds of the same makeup because of their tendency to isomerization, cyclization, and polymerization that often occur even in very mild conditions (low temperature, dilution, and so on).

This large class of natural compounds falls into monoterpenes sesquiterpenes ($C_{15}H_{24}$), diterpenes ($C_{20}H_{32}$), triterpenes ($C_{30}H_{48}$), tetraterpenes ($C_{40}H_{64}$), and polyterpenes ($C_{10}H_{16}$).

These numerous groups of compounds have been discovered virtually in all tissues and medicinal plants. They are found in essential oils (that contain monoterpenes and sesquiterpenes), amarines (mostly sesquiterpene lactones), resins, and balsams (containing diterpenes).

Terpenic compounds are actively involved in metabolic processes developing in a vegetational organism, an indication of which is their high reactivity. Some terpenoids regulate the activity of plant genes and have a chromatophoric system, can absorb radiant energy, and be involved in photochemical reactions. The carbon chains of some terpenoids are key intermediate products in biosynthesis of biologically active substances such as steroid hormones, enzymes, antioxidants, vitamins D, E, and K, and bile acids.

Terpenic compounds released by plants have been found to have a wide spectrum of biological effects, most of them have a low toxicity, and they are not known for a narrow specific effect—rather, their biological potential is distributed evenly among different systems and organs.

Terpenic compounds are associated with phytocidic activity of essential oils of many natural flora plants in different regions of the world. Many of these substances are harmful to diverse gram-positive and gram-negative microflora, some species of fungi, animalcula, and viruses.

Against the background of growing resistance germs of purulent infections are showing to antibiotics and the dominant significance of opportunistic microflora, the use of natural terpenoids becomes especially important today.

The gaseous medium in the sense of the present invention is any gaseous medium, for example, air, commercial oxygen or any mixture of gas and oxygen, carbon dioxide, and substances in the gaseous state, for example, water vapor.

The liquid medium is any liquid medium, such as water and water environments, for example, for fish breeding, aqueous or aqueous alcohol solutions, emulsions, suspensions, gel-like substances, liquid cosmetics such as lotions or creams, baby food, purees, beverages, and so on.

The solid medium is any solid medium, such as powders, granules, dry food mixes, sorbents, and so on.

The oxygen-containing gaseous medium in the sense of this invention is any gaseous medium, for example, air, commercial oxygen or any mixture of gas and oxygen, carbon dioxide, and substances in the gaseous state, for example, water vapor, that can be used for saturating various environments (see: above) with phyto-excretions.

Phyto-excretions can be removed by pumping an oxygen-containing medium through a closed chamber or by evacuating the gaseous medium from the chamber.

To obtain a purer oxygen-containing gaseous medium, it is preferred to purify it prior to saturation by pumping the flow of said medium through an additional chamber containing plants absorbing harmful impurities. For example, the following plants are well-suited for purifying the medium from:

Benzene (feedstock for many kinds of synthetic resin, a carcinogen): aglaonema, chlorophytum, chrysanthemums, dragon tree, epipremnum, gerbera, sansevieria, and spatiphillum;

Trichloroethylene (chloroform-smelling colorless liquid contained in varnishes and adhesives, a carcinogen): chamaedorea, chrysanthemums, dragon tree, epipremnum, Benjamin ficus, gerbera, ivy, sansevieria, and spatiphillum;

Formaldehyde (feedstock for artificial resins and adhesive base for mounting plates, a carcinogen): nephrolepis, marguerite, dragon tree, chamaedorea, Benjamin ficus, ivy, spatiphillum, schefflera, and dieffenbachia;

Xylene and toluene (used in polymer coatings): dieffenbachia, nephrolepis, anthurium, and Benjamin ficus; and Ammonia (a carcinogenic component of many nitrogen-containing industrial substances): anthurium, chrysanthemum frutescens, maranta, Benjamin ficus, dragon tree, and azalea.

The composition and quantity of substances absorbed and released by plants may be controlled by exposing the liquid and gaseous mediums and the plant to an additional effect of heat, electromagnetic radiation, light or sound, or variable atmospheric pressure.

For this purpose, the device used to carry out the present invention is provided with devices for atmospheric pressure variations or a different treatment of the plants.

BRIEF DESCRIPTION OF THE DRAWINGS

FIG. 1 is a general view of the claimed device.

DESCRIPTION OF THE PREFERRED EMBODIMENTS OF THE INVENTION

The device for treating a medium, such as a liquid medium, by saturating it with useful substances released by plants has the following design:

A vacuum compressor pump 1 is connected by gas pipes 2 at the delivery side thereof to a chamber or chambers 3 for a group of plants 4 absorbing harmful substances from the oxygen-containing medium, and by pipes 5 to a chamber or chambers 6 containing plants 7 that saturate the air with phyto-excretions (terpenoids), and also by pipes 8 to tanks 9 and 10 for saturating a liquid medium (water, liquid, and other liquid substances) 11 and to devices, such as condensers (coolers) 12 and 13 and a tank 14 for collecting (condensing) and accumulating useful ingredients. Chambers 3 and 6 for plants and tanks 9 and 10 are provided with devices 15 for controlling temperature, light, and other effects, and the gas pipes are provided with shutoff and other valves 16, and with discharge devices 17 for treating air and other mediums.

Vacuum compressor pump 1 is connected at the suction side thereof by gas pipes 18 to chamber or chambers 6 for plants releasing phyto-excretions, said chamber or chambers 6 being also connected to chambers 3 by pipes 19.

The device operates as follows:

At the start, the oxygen-containing gaseous medium is piped to chamber 3 filled with vegetating (intact) plants 4 that absorb harmful substances (benzenes, phenols, carbon monoxide, and so on) from the air to build up excess atmospheric pressure, whereupon the air mixture is delivered by gas pipes 2 to chamber 6 filled with vegetating (intact) or specially prepared (for example, incised) plants 7 to evacuate the air (or successively build up pressure and reduce it using vacuum compressor pump 1, and the air is saturated with phyto-excretions. Next, vacuum compressor pump 1 delivers the air mixture to discharge devices 17 for treating the gaseous and other mediums, and/or to tanks 9 and 10 where it is passed at different pressures through water, liquids, and/or other substances and, in this way, said water, liquids, and/or other substances are saturated with said useful phyto-excretions that are also collected by condensers (coolers) 12 and 13 and accumulated in respective tanks 14 under pressure for subsequent use.

EXAMPLE 1

The method described above was used to condense phyto-excretions from the air mixture in the chamber containing myrtle plants (*Myrtus communis* L.):
under pressure lowered periodically daily for the first four days over eight hours from 1.0 atm. to 0.5 atm. at a rate of up to 12 times an hour and temperature raised to +35° C.;
beginning with the fifth day, at constant normal pressure and temperature;* and
beginning with the fifth day, at normal temperature and pressure lowered periodically from 1 atm. to 0.8 atm. at a rate of six times an hour for eight hours.**

The experiments conducted showed that the volume of condensate and, therefore, the quantity of phyto-excretions released by the plants, under the effect of decreased atmospheric pressure and at increased air temperature grew by over 300% (see: Table 1). As the external conditions of the medium returned to normal, the condensable phyto-excretions were released at a rate of 50% above the starting rate for three to four days (see: column 2 in Table 1). Condensable phyto-excretions were still released at a rate of 250% to 300% of the starting rate in an embodiment in which evacuation was maintained periodically at a low rate (see: column 3 in Table 1).

The effect of reduced atmospheric pressure, therefore, stimulates significantly the release of condensable phyto-excretions (water and terpenoids).

EXAMPLE 2

The method described above was used to determine the quantity of terpenoids in the air mixture in a chamber containing myrtle plants (*Myrtus communis* L.):
under pressure lowered periodically daily for the first four days over eight hours from 1.0 atm. to 0.5 atm. at a rate of 12 times an hour and temperature raised to +35° C.;
beginning with the fifth day, at constant normal pressure and temperature;* and
beginning with the fifth day, at normal temperature and pressure lowered periodically from 1.0 atm. to 0.8 atm, at a rate of six times an hour over eight hours.**

The experiments conducted showed that the volume of released terpenoids under the effect of decreased atmospheric pressure and at increased air temperature grew by over 500% (see: Table 2). As the external conditions of the medium returned to normal, the release of terpenoids was still 25% above the starting rate for three to four days (see: column 2 in Table 2). Condensable phyto-excretions were still released at a rate of up to 400% of the starting rate in an embodiment in which evacuation was maintained periodically at a low rate (see: column 3 in Table 2).

The effect of reduced atmospheric pressure on the myrtle plants, therefore, stimulates significantly the release of terpenoids.

EXAMPLE 3

The method described above was used to condense phyto-excretions from the air mixture in a chamber containing myrtle plants (*Myrtus communis* L.):
under pressure raised periodically daily to 1.5 atm. followed by pressure lowered to 0.5 atm. (at a rate of five minutes under increased pressure and reduced pressure) for the first four days over eight hours at a rate of six time an hour and temperature raised to +35° C.;
beginning with the fifth day, at constant normal pressure and temperature;* and
beginning with the fifth day, at normal temperature and pressure raised and lowered periodically up to 1.5 atm. and down to 0.5 atm. at a rate of six times an hour over eight hours.**

The experiments conducted showed that the volume of condensate and, therefore, the quantity of phyto-excretions released by the plants under the effect of pressure increased and decreased periodically and at increased air temperature grew by over 300% (see: Table 3). As the external conditions of the medium returned to normal, the release of condensable phyto-excretions was still 50% above the starting rate for three to four days (see: column 2 in Table 3). Condensable phyto-excretions were still released at a rate of 250% to 300% of the starting rate in an embodiment in which pressure was increased and decreased periodically (see: column 3 in Table 3).

The effect of reduced atmospheric pressure on the plants, therefore, stimulates significantly the release of condensable phyto-excretions (water and terpenoids).

EXAMPLE 4

The method described above was used to measure absorption of carbon dioxide from the air mixture in a chamber containing myrtle plants (*Myrtus communis* L.) under pressure raised periodically daily over eight hours from 1.0 atm. to 1.2 atm. at a rate of 12 times an hour.

The experiments conducted (see: Table 4) showed that absorption of carbon dioxide by myrtle plants grows by more than 40% under the effect of increased atmospheric pressure. Accordingly, release of oxygen increases as well.

TABLE 1

Effect of Artificial Periodic Reduction in Ambient Air Pressure on the Intensity of Condensation of Phyto-Excretions of Myrtle Plants

| Experiment day | Condensation intensity* (beginning with the 5th day without artificial pressure reduction to maintain excretion) Prior to/at the end of treatment, g/hr/dm$^2$ | Condensation intensity** Prior to/at the end of treatment, g/hr/dm$^2$ |
| --- | --- | --- |
| 1 | 1.2/5.1 | 1.2/5.1 |
| 2 | 3.8/7.7 | 3.8/6.7 |
| 3 | 4.1/8.5 | 4.1/7.5 |

TABLE 1-continued

Effect of Artificial Periodic Reduction in Ambient Air Pressure on the Intensity of Condensation of Phyto-Excretions of Myrtle Plants

| Experiment day | Condensation intensity* (beginning with the 5th day without artificial pressure reduction to maintain excretion) Prior to/at the end of treatment, g/hr/dm$^2$ | Condensation intensity** Prior to/at the end of treatment, g/hr/dm$^2$ |
|---|---|---|
| 4 | 4.1/8.4 | 4.1/7.4 |
| 5 | 3.5 | 3.5/4.5 |
| 6 | 2.4 | 3.4/4.5 |
| 7 | 1.8 | 3.5/4.5 |

Note:
The differences are significant on the 1st Student criterion (95% significance level).

TABLE 2

Effect of Artificial Periodic Reduction in Ambient Air Pressure on the Intensity of Release of Terpenoids by Myrtle Plants

| Experiment day | Intensity of release of terpenoids* Control (beginning with the 5th day without artificial pressure reduction to maintain excretion) Prior to/at the end of daily treatment, mg/hr/dm$^2$ | Intensity of release of terpenoids ** Prior to/at the end of daily treatment, mg/hr/dm$^2$ |
|---|---|---|
| 1 | 8/29 | 8/29 |
| 2 | 15/37 | 15/37 |
| 3 | 19/45 | 19/45 |
| 4 | 20/47 | 20/47 |
| 5 | 15 | 19/32 |
| 6 | 14 | 19/28 |
| 7 | 10 | 19/29 |

Note:
The differences are significant on the 1st Student criterion (95% significance level).

TABLE 3

Effect of Artificial Periodic Increase and Reduction in Ambient Air Pressure on the Intensity of Condensation of Phyto-Excretions of Myrtle Plants

| Experiment day | Condensation intensity* (beginning with the 5th day without artificial pressure reduction to maintain excretion) Prior to/at the end of treatment, g/hr/dm$^2$ | Condensation intensity** Prior to/at the end of treatment, g/hr/dm$^2$ |
|---|---|---|
| 1 | 1.2/5.5 | 1.2/5.6 |
| 2 | 3.8/7.7 | 3.8/7.5 |
| 3 | 4.1/8.5 | 4.1/8.4 |
| 4 | 4.1/8.4 | 4.1/8.3 |
| 5 | 3.5 | 3.5/5.1 |
| 6 | 2.4 | 3.4/5.1 |
| 7 | 1.8 | 3.5/5.1 |

Note:
The differences are significant on the 1st Student criterion (95% significance level).

TABLE 4

Effect of Artificial Periodic Increase in Ambient Air Pressure on the Intensity of $CO_2$ Absorption by Myrtle Plants

| Experiment day | Photosynthesis intensity* Under normal pressure and air temperature (+25° C.) mg/hr/dm$^2$ | Photosynthesis intensity** Under increased air pressure (+0.2 atm.) mg/hr/dm$^2$ |
|---|---|---|
| 1 | 7.2 | 9.5 |
| 2 | 7.0 | 9.7 |
| 3 | 7.4 | 10.5 |
| 4 | 6.9 | 10.1 |
| 5 | 7.1 | 10.4 |
| 6 | 7.2 | 10.6 |
| 7 | 6.8 | 10.0 |

Note:
The differences are significant on the 1st Student criterion (95% significance level).

What is claimed is:

1. A method for treating a medium by saturating it with useful substances released by plants, comprising supplying a gaseous medium into a chamber containing vegetating or cut plants and passing the gaseous medium saturated with phyto-excretions through the medium being treated, wherein the pressure of said gaseous medium in the chamber containing vegetating or cut plants is reduced periodically or raised and then reduced periodically.

2. The method of claim 1, wherein the gaseous medium is delivered initially into another chamber containing plants that absorb harmful substances and excess pressure of said gaseous medium is built up therein.

3. The method of claim 1, wherein the medium being treated is a gaseous medium, or a liquid, or a solid medium such as powder, or granules, or sorbent.

4. A device for treating a medium by saturating it with useful substances released by plants, comprising means for pumping a gaseous medium to at least one chamber for plants releasing phyto-excretions that is connected by a pipeline to said means at the suction side thereof, said means being connected at the delivery side thereof to at least one receptacle for the medium being treated, wherein at least one chamber for plants releasing phyto-excretions is also connected by a pipeline to the pumping means at the delivery side thereof.

5. The device of claim 4, further provided with at least one chamber for plants absorbing harmful substances that is connected by pipelines to the chamber for plants releasing phyto-excretions and to said pumping means at the delivery side thereof.

6. The device of claim 4, wherein the receptacle for the medium being treated is a tank or a room.

* * * * *